US012145918B2

(12) United States Patent
Tan et al.

(10) Patent No.: US 12,145,918 B2
(45) Date of Patent: Nov. 19, 2024

(54) CROSSLINKABLE MESOGENIC DIANHYDRIDE MONOMERS

(71) Applicant: Government of the United States, as represented by the Secretary of the Air Force, Wright-Patterson AFB, OH (US)

(72) Inventors: Loon-Seng Tan, Centerville, OH (US); Zhenning Yu, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 55 days.

(21) Appl. No.: 18/299,092

(22) Filed: Apr. 12, 2023

(65) Prior Publication Data

US 2024/0101525 A1 Mar. 28, 2024

Related U.S. Application Data

(60) Provisional application No. 63/406,012, filed on Sep. 13, 2022.

(51) Int. Cl.
*C07D 307/89* (2006.01)

(52) U.S. Cl.
CPC .................. *C07D 307/89* (2013.01)

(58) Field of Classification Search
CPC .................................................... C07D 307/89
See application file for complete search history.

(56) References Cited

U.S. PATENT DOCUMENTS

| | | | |
|---|---|---|---|
| 5,196,506 A | 3/1993 | Tamai et al. | |
| 5,606,014 A | 2/1997 | Connell et al. | |
| 6,124,035 A | 9/2000 | Connell et al. | |
| 6,350,817 B1 | 2/2002 | Connell et al. | |
| 10,988,437 B1 | 4/2021 | Tan et al. | |
| 11,608,310 B1 | 3/2023 | Tan et al. | |
| 2015/0275089 A1* | 10/2015 | Katano | C08G 73/1067 427/520 |
| 2021/0187902 A1* | 6/2021 | Fujiwara | C09K 19/0403 |

FOREIGN PATENT DOCUMENTS

| | | | |
|---|---|---|---|
| JP | 2000248252 A | | 9/2000 |
| JP | 2009079008 A | * | 4/2009 |

OTHER PUBLICATIONS

Human-Assisted Machine Translation of Chemical Reagents, 2009, 31(9), 673-676 (Year: 2009).*
Chemical Reagents, 2009, 31(9), 673-676 (Year: 2009).*
JP-2009079008-A Machine Translation (Year: 2009).*
Pyrolysis of Organic Molecules, Second Edition, 2019, Chapter 12, pp. 483-553 (Year: 2019).*
U.S. Appl. No. 18/299,090, filed Apr. 12, 2023.
U.S. Appl. No. 18/299,096, filed Apr. 12, 2023.
U.S. Appl. No. 18/299,100, filed Apr. 12, 2023.
U.S. Appl. No. 18/299,353, filed Apr. 12, 2023.
U.S. Appl. No. 18/299,375, filed Apr. 12, 2023.
Nye, S. A.: Polyimides synthesized from 4,4'-(1,2-ethynediyl)bis(phthalic anhydride). Journal of Polymer Science, Part A: Polymer Chemistry 1990, 28, 2633-40.
Pardey, R.; Zhang,A.; Gabori, P. A.; Harris, F. W.; Stephen Z. D. Cheng, S. Z. D.; Jerry Adduci, J.; Facinelli, J. V.; Lenz, R. W.; Monotropic Liquid Crystal Behavior in Two Poly(ester imides)with Even and Odd Flexible Spacers Macromolecules 1992, 25, 5060-5068.
Inoue, T.; Kakimoto, M.-A.; Imai, Y.; Watanabe, J.: First Observation of a Thermotropic Liquid Crystal in a Simple Polyimide Derived from 1,11-Diaminoundecane and 4,4"—Terphenyltetracarboxylic Acid. Macromolecules 1995, 28, 6368-6370.
Inoue, T.; Kumagai, K.; Kakimoto, M.; Imai, Y.; Watanabe, J.; High-Pressure Synthesis and Properties of Aliphatic-Aromatic Polyimides via Nylon-Salt-Type Monomers Derived from Aliphatic Diamines with Pyromellitic Acid and Biphenyltetracarboxylic Acid Macromolecules 1997, 30, 1921-1928.
Kaneko, T. I. Imamura, K.: Watanabe, J.; Reversible Crystal Deformation Observed in the Main-Chain Type of Liquid Crystalline Polyimide, Macromolecules 1997, 30, 4244-4246.
Sato, M.; Ujiie, S.; Tada, Y.; Kato, T. Semirigid: Homo- and Copoly(Imide-Carbonate)s Based on 3,4,3 ,4-p-Terphenyltetracarboxdiimide. High Performance Polymers 1998, 10, 155-162.
Fernberg, P; Guan Gong, G.; Mannberg, P.; Tsampas, S.; Development of novel high Tg polyimide-based composites. Part I: RTM processing properties Journal of Composite Materials 2018, vol. 52(2) 253-260.
Abbott, A.; Gibson, T.; Tandon, G. P.; Hu, L.; Avakian, R.; Baur, J.; Koerner, H.: Melt extrusion and additive manufacturing of a thermosetting polyimide. Additive Manufacturing 2021, 37, 101636.
Zhang, H.; Wang, W.; Chen, G.; Zhang, A.; Fang, X.: Melt-Processable Semicrystalline Polyimides Based on 1,4-Bis(3,4-dicarboxyphenoxy)benzene Dianhydride (HQDPA): Synthesis, Crystallization, and Melting Behavior. Polymers 2017, 9.
Noël, C.; Navard, P.: Liquid crystal polymers. Progress in Polymer Science 1991, 16, 55-110.
Connell, J. W.; Smith, J. G., Jr.; Hergenrother, P. M.: Oligomers and polymers containing phenylethynyl groups. Journal of Macromolecular Science, Reviews in Macromolecular Chemistry and Physics 2000, C40, 207-230.

(Continued)

*Primary Examiner* — Mark V Stevens
*Assistant Examiner* — Daniel John Burkett
(74) *Attorney, Agent, or Firm* — AFMCLO/JAZ; James F. McBride (57) ABSTRACT

Applicants disclose a family of rod-like dianhydrides that contain two phthalic anhydride moieties linked by a bridge that is comprised of at least one ethynyl and one paraphenylene group and processes of making and using such rod-like dianhydrides. Such rod-like dianhydrides can endow net-work structures with improved mechanical and thermal properties in the crosslinked-polymer products.

3 Claims, 2 Drawing Sheets

(56) References Cited

OTHER PUBLICATIONS

Smith, J. G., Jr.; Connell, J. W.: Chemistry and properties of imide oligomers from phenylethynyl-containing diamines. High Performance Polymers 2000, 12, 213-223.
Connell, J. W.; Smith, J. G., Jr.; Hergenrother, P. M.: Properties of imide oligomers containing pendent phenylethynyl groups. High Performance Polymers 1997, 9, 309-321.
Kricheldorf, H. R.: Liquid-crystalline polyimides. Advances in Polymer Science 1999, 141, 83-187.
Takeichi, T.; Tanikawa, M.; Internal Acetylene Unit Linked para to the Aromatic Ring as a Crosslink Site for Polyimide Journal of Polymer Science: Part A: Polymer Chemistry, 1996, vol. 34, 2205-2211.
Meng, Y. Z.; Tjong, S. C.; Hay, A. S.; Morphology, rheological and thermal properties of the melt blends of poly (phthalazinone ether ketone sulfone) with liquid crystalline co polyester Polymer 1998, vol. 39, No. 10, pp. 1845-1850.
Guan, Q.; Picken, S. J.; Sheiko, S. S.; Theo J. Dingemans, T. J.; High-Temperature Shape Memory Behavior of Novel All Aromatic (AB)n-Multiblock Copoly(ester imide)s Macromolecules 2017, 50, 3903-3910.
Liu, S. L.; Chung, T. S.; Geng, J. X.; Zhou, E. L.; Tamai, S.; Phase Transition and Transition Kinetics of a Thermotropic Poly(amide-imide) Derived from 70% Pyromellitic Dianhydride, 30% Terephthaloyl Chloride, and I ,3-Bis [4-(4'-aminophenoxy)cumyl]benzene Macromolecules 2001, 34, 8710-8719.
Guan, Q.; Norder, B.; Chu, L.; Besseling, N. A. M.; Picken, S. J.; Theo J. Dingemans, T. J.; All-Aromatic (AB)n-Multiblock Copolymers via Simple One-Step Melt Condensation Chemistry Macromolecules 2016, 49, 8549-8562.
Tamboli, A. B.; Ghodke, S. D.; Diwate, A. V.; Joshi, M. D.; Ubale, V. P.; Maldar, N. N.: Processable poly (ether ether ketone imide)s. High Performance Polymers 2021, DOI: 10.1177/09540083211055044.
U.S. Appl. No. 16/752,794.
U.S. Appl. No. 16/752,804.
U.S. Appl. No. 18/103,860.
Asanuma, T.; Oikawa, H.; Ookawa, Y.; Yamasita, W.; Matsuo, M.; Yamaguchi, A.: Synthesis of thermotropic liquid crystal polyimide and its properties. Journal of Polymer Science, Part A: Polymer Chemistry 1994, 32, 2111-18.
Zheng, B.; Ree, B.; Yu, Z.; Tan, L.; Koerner, H.; Development of high-performance nematic liquid crystalline polyimides (LCPI) for 3D printing, Presentation Aug. 2022.

\* cited by examiner

CROSSLINKABLE MESOGENIC DIANHYDRIDE MONOMERS

RIGHTS OF THE GOVERNMENT

The invention described herein may be manufactured and used by or for the Government of the United States for all governmental purposes without the payment of any royalty.

CROSS-REFERENCE TO RELATED APPLICATION

The present application claims priority to U.S. Provisional Application Ser. No. 63/406,012 filed Sep. 13, 2022, the contents of which is hereby incorporated by reference in their entry. The present application is related to, but does not claim priority to, U.S. application Ser. No. 14/999,921 which was filed under a secrecy order on Jan. 25, 2017.

FIELD OF THE INVENTION

The present invention relates to a family of rod-like dianhydrides that contain two phthalic anhydride moieties linked by a bridge that is comprised of at least one ethynyl and one paraphenylene group and processes of making and using such rod-like dianhydrides.

BACKGROUND OF THE INVENTION

Applicants disclose a family of rod-like dianhydrides that contain two phthalic anhydride moieties linked by a bridge that is comprised of at least one ethynyl and one paraphenylene group and processes of making and using such rod-like dianhydrides. These aromatic and conjugated dianhydrides possess the structural requirements of (a) being mesogenic that can endow melt-extrusion improving thermotropic liquid-crystallinity in highly aromatic polyimides when polymerized with liquid-crystallinity (LC)-enabling diamines, such as 1,3-bis[4-(4'-aminophenoxy)cumyl]benzene (BACB) and α,ω-bis(4-aminophenoxy)-containing arylether compounds (MPDA), and (b) being thermally crosslinkable that can endow net-work structures with improved mechanical and thermal properties in the crosslinked-polymer products.

SUMMARY OF THE INVENTION

Applicants disclose a family of rod-like dianhydrides that contain two phthalic anhydride moieties linked by a bridge that is comprised of at least one ethynyl and one paraphenylene group and processes of making and using such rod-like dianhydrides. Such rod-like dianhydrides can endow net-work structures with improved mechanical and thermal properties in the crosslinked-polymer products.

Additional objects, advantages, and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

As used herein, the words "about," "approximately," or the like, when accompanying a numerical value, are to be construed as indicating a deviation as would be appreciated by one of ordinary skill in the art to operate satisfactorily for an intended purpose.

As used herein, the words "and/or" means, when referring to embodiments (for example an embodiment having elements A and/or B) that the embodiment may have element A alone, element B alone, or elements A and B taken together.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

BACB is the abbreviation for "1,3-bis[4-(4'-aminophenoxy)cumyl]benzene" moiety.

DPA is the abbreviation for Di-(Phthalic Dianhydride).

EDPA is the abbreviation for compound with a chemical name of "ethynyl-4,4'-di(phthalic anhydride)."

EFPE-DPA is the abbreviation for compound with a chemical name of "4,4'-(2-fluoro-1,4-phenylene)bis(ethyne-2,1-diyl)diphthalic anhydride."

1,4EPE-DPA is the abbreviation for compound with a chemical name of "4,4'-(1,4-phenylenebis(ethyne-2,1-diyl)) diphthalic anhydride."

1,3EPE-DPA is the abbreviation for compound with a chemical name of "4,4'-(1,3-phenylenebis(ethyne-2,1-diyl)) diphthalic anhydride."

EPPE-DPA is the abbreviation for compound with chemical names of "4'-((3,4-dicarboxyphenyl)ethynyl)biphenyl-3,4-dicarboxylic dianhydride," and "4,4'-(biphenyl-4,4'-diyl-bis(ethyne-2,1-diyl))diphthalic anhydride."

LC is the abbreviation for liquid-crystalline or liquid-crystallinity.

MPDA is the abbreviation for multi-phenoxy-linked 4,4'-dianiline.

PE-DPA is the abbreviation for compound with a chemical name of "4'-((3,4-dicarboxyphenyl)ethynyl)biphenyl-3,4-dicarboxylic dianhydride."

R-DPA is the abbreviation for Reactive Di-(Phthalic Dianhydride).

TPDA is the abbreviation for compound with a chemical name of "terphenyl-3,3",4,4"-dianhydride".

TLC is the abbreviation for thermal crystalline or thermal crystallinity.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Figure 1:
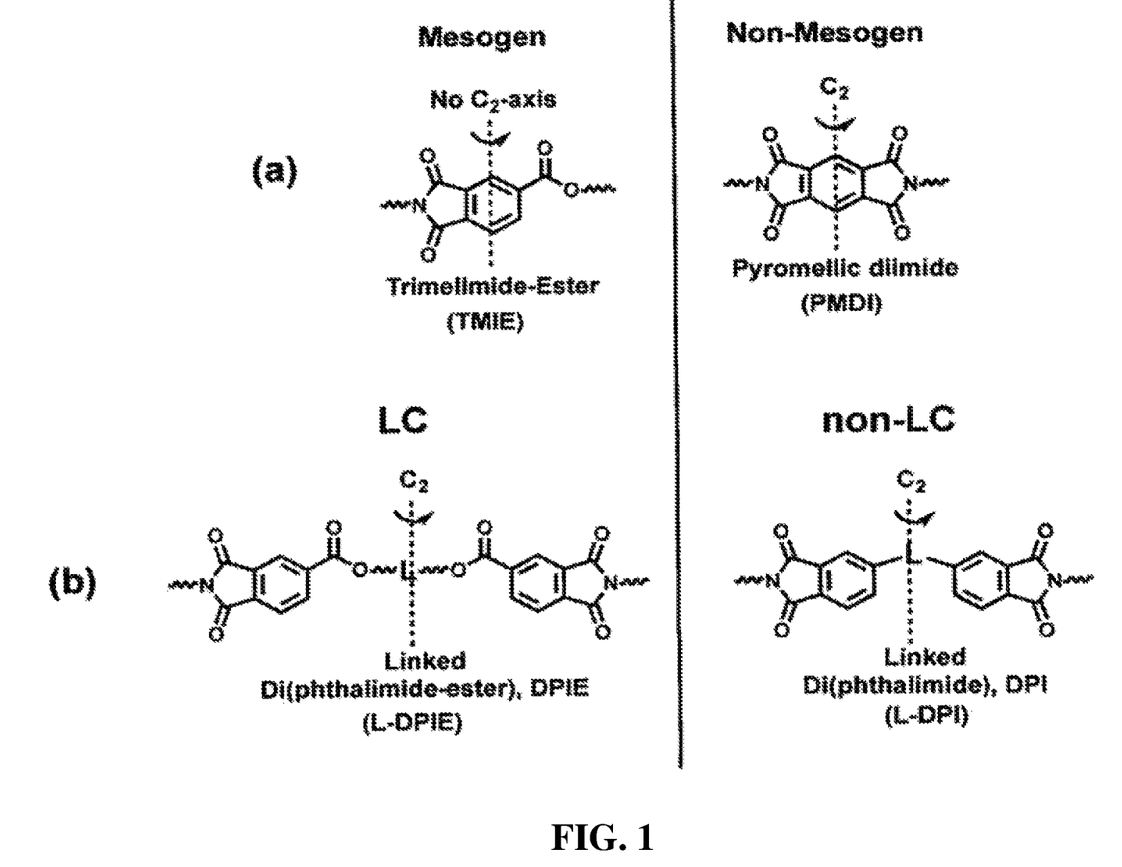
FIG. 1 depicts the structural comparisons of (a) an unsymmetrical trimellitic imide-ester, TMIE and a symmetrical diimide, PMDI and (b) the corresponding repeat units in their polyimides that are liquid crystalline or not. L is traditionally small molecular moieties such as nil, —O—, $>C=O$, $>SO_2$, $>C(CF_3)_2$ and the wavy symbol represent flexible chains such as $(CH_2)_n$, —$(CH_2CH_2O)_n$.

A special class of thermotropic liquid-crystalline polymer (TLCP) is the main-chain polyimides (PI) which are typically synthesized from the polycondensation of an aromatic dianhydride and a diamine. These traditional thermotropic liquid-crystalline polyimides (TLCP-PI) are constituted by (i) the rigid dianhydride being the mesogen capable of self-aggregation to form the so-called liquid-crystalline (LC) phase, i.e., a mesophase which is a phase between crystal and isotropic melt phases; (ii) the diamine being the flexible and thermally mobile to facilitate the self-aggregation of the mesogenic units. From the structural standpoint of mesogenic anhydrides, there are generally two approach to the synthesis of thermotropic liquid-crystalline polyimides (TLC-PI), namely the utilization of mesogens that are either symmetrical dianhydrides such as pyromellitic dianhydride (PMDA), 3,4,3',4'-biphenyltetracarboxylic dianhydride (BPDA) and TPDA whose symmetry is defined by having a $C_2$-rotation molecular axis and unsymmetrical di(anhydride-ester) with the generic structure, AE-L-AE, in which the AE is an unsymmetrical anhydride, and L is a bivalent linking group (see FIG. 1 for the corresponding imide structures). Other symmetrical dianhydrides are 3,4,3',4'-benzophenone tetracarboxylic dianhydride (BTDA), 3,4,3',4'-diphenylsulfone tetracarboxylic dianhydride (BSDA) and 4,4'-oxy-di(phthalic anhydride) (ODPA). There have been a number of systematic studies conducted on the syntheses and TLC correlation of various aromatic-aliphatic semirigid polyimides composed of these symmetrical dianhydrides and aliphatic chains in the main chains. A general finding is that most of them are crystalline; and because of their poor mesogenic properties, they are unable to show TLC properties without the inclusion of a traditional biphenyl mesogen in the polymer backbones; thus poly(ester-imides) and poly(carbonate-imides) that were composed of asymmetric N-phenylphthalimide rings form LC phases. For examples, the work of M. Sato, et al., High Performance Polymers, 1998, 10, 155-162, and that of T. Inoue, et al. Macromolecules 1995, vol. 28, pp. 6368-6370, have shown that the thermotropic liquid crystals for the simple polyimides which consist of symmetrical imide rings and polymethylene spacers appear to be only that derived from TPDA and 1,11-diaminoundecane.

Pyromellitic dianhydride (PMDA) is a common, structurally rigid dianhydride, and the key building block for the well-known aromatic polyimide, namely Kapton, which is a semi-crystalline polymer. As illustrated by the work of H. R. Kricheldorf, et al. Makromolekulare Chemie, 1993, vol. 194, pp 1209-24, and that of M. Sato, et al. Polymer Journal 2002, vol. 34, pp. 158-165, while PMDA meets the structural rigidity of being an LC mesogen, a large number of polyimides and poly(ester-mide)s derived from PMDA and aliphatic components only form isotropic (non-LC) melts. Therefore, it was rather unusual that a thermotropic liquid-crystalline polyimide (TLC-PI) was reported in 1994 by Asanuma et al. Journal of Polymer Science, Part A: Polymer Chemistry 1994, 32, 2111-18. This particular polyimide, designated as PMDA-BACB, was synthesized from PMDA and a highly aromatic but flexible diamine, namely, 1,3-bis [4'-(4"-aminophenoxy)cumyl]benzene (BACB).

However, while PMDA-BACB polyimide is a thermotropic liquid crystalline polymer, its LC phase can be achieved at temperatures well above 300° C. and the associated melt viscosity is deemed impractical for the 3D-printing of thermosetting polyimides. These processing issues are stemming from the exceeding strong propensity of the PMDA moieties to aggregate. Therefore, there is a need for non-PMDA dianhydrides that can lead to LC phase at or below 300° C. and are capable of thermal crosslinking at temperatures after LC transition temperatures.

Non-PMDA mesogenic dianhdrides with higher aspect ratios: A special family of rigid dianhydrides is based on α,ω-diphthalic dianhydride (DPA) motif, designated here as L(DPA), with the generic structure below:

and formula as PA-L-PA, where PA is phthalic anhydride and L is direct bond or an aromatic and/or conjugated connector. The simplest L(DPA) dianhydride, namely, BPDA (3,3',4,4'-biphenyltetracarboxylic dianhydride; L=direct bond) is not mesogenic even when combined with the very flexible aliphatic, α,ω-$(CH_2)_n$, chains to enable the resulting polyimides to be thermotropic liquid-crystalline (TLC). As shown in our work, when the two PA units are connected by the most rigid two-carbon unit, namely the ethynyl bridge, the resulting ethynyl-diphthalic dianhydride) or EDPA in combination with the LC-promoting, highly aromatic diamine BACB, the resulting polyimide, EDPA-BACB is also not mesogenic.

However, when the two PA units are connected by a longer paraphenylene bridge, the resulting "higher-aspect-ratio" dianhydride, namely, TPDA (3,3',4,4'-p-terphenyltetracarboxdianhydride; L=paraphenylene) and diamines containing similar aliphatic chains did indeed result in TLC-polyimides, as shown by the work of M. Sato, et al. Macromolecular Chemistry and Physics 1996, vol. 197, pp. 2765-2774.

Mesogenic Dianhydrides, R-DPA: Our non-PMDA mesogens belong to a family of aromatic rod-like dianhydrides with the general composition and structure of where PA is phthalic anhydride and L is rigid connector such as an ethynyl (E), a paraphenylene (P), or a rigid moiety constituted by a P-E combination; L can be divided into a reactive (R) group that contains one or more thermally reactive ethynyl (E) units, and non-reactive (NR) group when L does not contain any ethynyl (E) unit.

Figure 2:
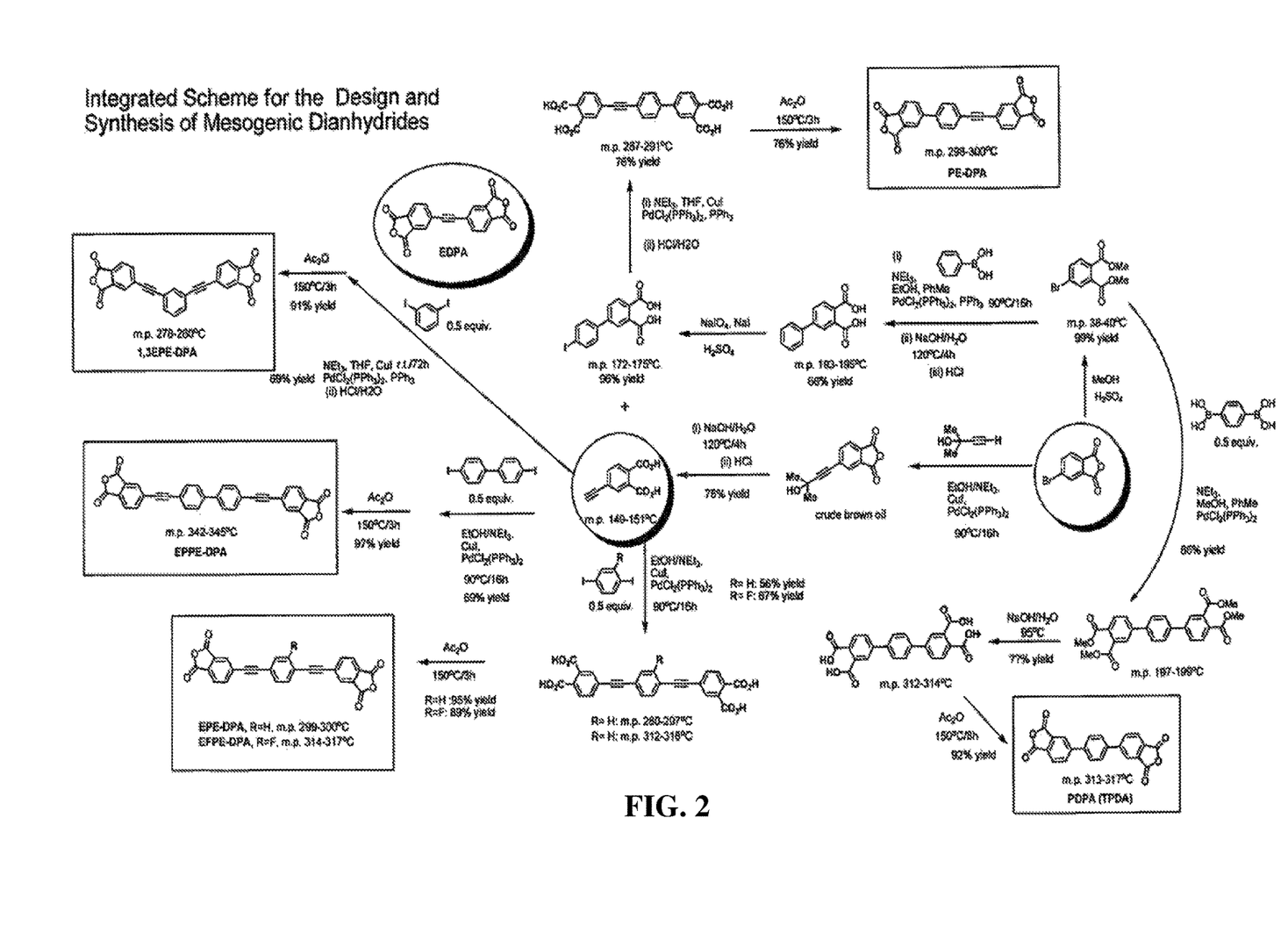
FIG. 2 depicts an integrated scheme for the design and synthesis of new reactive mesogenic dianhydrides, R-DPA's: (i) PE-DPA (ii) 1,4EPE-DPA (iii) EFPE-DPA and (iv) EPPE-DPA. The dianhydrides EDPA (ethynyl-linked) and PDPA (paraphenylene-linked; same as TPDA) are known compounds). 1,3EPE-DPA is a new dianhydride and synthesized to demonstrate the adverse effect of kink on the dianhydride's mesogenicity.

Mesogenic Dianhydride Synthesis: With reference to FIG. 2, an integrated scheme was devised for the design and synthesis of new mesogenic dianhydrides: (i) PE-DPA (ii) 1,4P2E-DPA (iii) 1,4FP2E-DPA and (iv) 1,4-BP2E-DPA. The dianhydrides EDPA (ethynyl-linked) and PDPA (paraphenylene-linked; same as TPDA) are known compounds). 1,3P2E-DPA is a new dianhydride and synthesized to demonstrate the adverse effect of kink on the dianhydride mesogenicity. In our synthetic strategy for the intergrated scheme, 4-bromophthalic anhydride and 4-ethynylphthalic anhydride play the role of starting point and the key intermediate that can be branched into the divergent synthetic routes to all the dianhydrides, including EPDA which is commercially available. The key reactions employed are (i) Pd—Cu bicatalyzed Sonogashira reaction to couple an arylenthynyl and an arylbromide or an aryliodide; (ii) Pd-catalyzed Suzuki reaction to couple an arylbromide and an arylboronic acid; (iii) protection and deprotection of an aromatic ortho-diacids with methylester functions; (iv) chemical imidization effected by acetic anhydride and pyridine.

Rod-Like Dianhydrides and Processes of Making and Using Same.

For purposes of this specification, headings are not considered paragraphs. In this paragraph, Applicants disclose a monomer having the following structure:

wherein X has one of the following formula:

In this paragraph, Applicants disclose a process of making a monomer, said process comprising:

a.) thermally dehydrating, at temperature from about 150° C. to about 200° C., preferably from about 150° C. to about 180° C. a molecule or a mixture of molecules having the following formula:

-continued

10 or
b.) chemically dehydrating a molecule or a mixture of molecules having the following formula:

by contacting said molecule or mixture of molecules with acetic anhydride. Said process can produce the monomer of the preceding paragraph.

In this paragraph, Applicants disclose molecules having the following structures:

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1 4,4'-(1,4-phenylenebis(ethyne-2,1-diyl))diphthalic anhydride (EPE-DPA)(a) Synthesis of 4-ethynylphthalic acid: In a 500 mL round-bottomed flask equipped with a magnetic stir bar and a condenser connected to a nitrogen inlet, 22.70 g (0.10 mol) of 4-bromophthalic anhydride was dissolved in 200 mL of ethanol. To this solution, 55.8 mL of trimethylamine was added slowly. The resulting solution was stirred at room temperature for 1 hour and then 16.82 g (0.20 mol) of 2-methyl-3-butyn-2-ol, 0.35 g (0.50 mmol) of bis(triphenylphosphine)palladium dichloride, and 95.2 mg (0.50 mmol) of copper iodide were added. The reaction mixture was placed in a preheated oil bath at 90° C. and heated at that temperature for 16 hours. After the reaction vessel had been removed from the oil bath and allowed to cool to room temperature, ethanol and excess triethylamine were removed from the product mixture by rotary evaporation. 200 mL of acetone was added to extract the ethynylated product. The white insolubles (mostly NEt$_3$HBr) were removed by filtration. After the removal of acetone from the filtrate by rotary evaporation, the crude product was a dark brownish viscous liquid. To this liquid, 12.00 g (0.30 mol) of sodium hydroxide in 300 mL water was added. The resulting mixture was placed in an oil bath that had been preheated to 120° C., and heated at that temperature for 4 hours. During this period of time, about 250 mL of aqueous liquid was distilled off. After cooling to room temperature, 200 mL of water was added to the mixture. Solids were removed via filtration. The filtrate was neutralized with concentrated hydrochloric acid to pH around 2. The liquid phase was extracted with 3×150 mL of ethyl acetate. The ethyl acetate extract was washed with 3×150 mL of de-ionized water. After ethyl acetate had been removed by rotary evaporation, the residues was dissolved in hexanes/ethyl acetate (1:1) and the resulting solution was passed through a short silica gel column. After solvents had been removed, the crude product was obtained as light yellow solids. The crude product was boiled in 100 mL of hot toluene for a few minutes, and filtrated after cooling to room temperature. 14.90 grams, 78.4% isolated yield of desired product was obtained as near white powder, m.p. 148.6-151.0° C. $^1$H NMR (400 MHz, d$_6$-acetone): δ=7.82-7.83 (d, J=1.6 Hz, 1H), 7.78-7.81 (d, J=8.0 Hz, 1H), 7.70-7.73 (dd, J=8.0, 1.6 Hz, 1H), 3.90 (s, 1H). (b) Synthesis of 4,4'-(1,4-phenylenebis(ethyne-2,1-diyl))diphthalic acid: To a 300 mL round-bottomed flask equipped with a magnetic stir bar and a condenser connected to a nitrogen inlet, 12.00 g (63.0 mmol) of 4-ethynylphthalic acid, 9.90 g (30.0 mmol) of 1,4-diiodobenzene, 210.6 mg (0.3 mmol) of bis(triphenylphosphine)palladium dichloride and 57.1 mg (0.3 mmol) of copper iodide ethanol were charged. The flask was subjected to three cycles of "vacuuming and back-filling with nitrogen"; then, 30 mL of trimethylamine and 120 mL of acetonitrile were added. The mixture was heated in an oil bath at 40° C. for 4 hours. After cooled to room temperature, acetonitrile and excess triethylamine were removed under vacuum, and the residue was re-dissolved in 500 mL of water. Insoluble particles were removed via filtration. The filtrate was neutralized with concentrated hydrochloric acid to pH around 2. Solid product was collected by filtration and washed with de-ionized water. After air drying, the solids were washed with 200 mL ethyl acetate and 100 mL ethanol, and finally air-dried. 7.04 grams of product was obtained as yellow powder, 51.7% isolated yield, m.p. 279.6-297.1° C. $^1$H NMR (400 MHz, d$_6$-acetone): δ=7.92 (d, J=1.6 Hz, 2H), 7.85-7.87 (d, J=8.0 Hz, 2H), 7.78-7.87 (dd, J=8.0, 1.6 Hz, 2H), 7.68 (s, 4H). (c) Synthesis of 4,4'-(1,4-phenylenebis(ethyne-2,1-diyl))diphthalic anhydride (EPE-DPA): To a 100 mL round-bottomed flask equipped with a magnetic stir bar and a condenser connected to a nitrogen inlet, 7.04 g (15.5 mmol) of 4,4'-(1,4-phenylenebis(ethyne-2,1-diyl)) diphthalic acid and 50 mL of acetic anhydride were added. The reaction mixture was subject to heating in an oil bath at 150° C. for six hours. After cooling to room temperature, the reaction mixture was filtered, the solid product was collected and washed with hexanes. After vacuum drying at 150° C. and 0.5 torr in vacuum oven for 24 hours, 6.18 grams (95.3% isolated yield) of product was obtained as yellowish green crystals, m.p. 298.7-300.4° C. $^1$H NMR (400 MHz, d$_6$-acetone): δ=8.22 (dd, J=0.8, 1.2 Hz, 2H), 8.17-8.19 (dd, J=1.2, 7.6 Hz, 2H), 8.12-8.14 (dd, J=0.8, 7.6 Hz, 2H), 7.68 (s, 4H). FT-IR (cm 1): 3069, 3039, 3015, 2213, 1839, 1818, 1770, 1610, 1514, 1430, 1610, 1514, 1430, 1409, 1315, 1258, 1242, 1137, 1106, 1079, 930, 890, 869, 836, 734, 670, 532, 514, 445, 421. Elemental analysis calculated for $C_{26}H_{10}O$: C, 74.64; H, 2.41; O, 22.95. Found: C, 74.69; H, 2.32; O, 22.98.

Example 2 4,4'-(2-fluoro-1,4-phenylene)bis(ethyne-2,1-diyl)diphthalic anhydride (EFPE-DPA). (a) Synthesis of 4,4'-(2-fluoro-1,4-phenylene)bis(ethyne-2,1-diyl)diphthalic acid: To 300 mL round-bottomed flask equipped with a stir bar and a condenser connected to a nitrogen inlet, 12.55 g (66.0 mmol) of 4-ethynylphthalic acid, 10.44 g (30.0 mmol) of 2-fluoro-1,4-diiodobenzene, 210.6 mg (0.30 mmol) of bis(triphenylphosphine)palladium dichloride and 57.1 mg (0.3075 mmol) of copper iodide were charged. The flask was subject to three cycles of "vacuuming then back-filling with nitrogen", 30 mL of triethylamine and 90 mL of ethanol were then added. The reaction mixture was stirred at room temperature for 96 hours before ethanol and excess triethylamine were removed by rotary evaporation. Then, 600 mL of water was added and the resulting mixture was filtered. The filtrate was neutralized with hydrochloric acid until pH is lower than 2. The precipitated tetraacid was collected via filtration, and air dried. The dried crude product was then washed with 50 mL of 2-propanol and 300 mL of ethyl acetate. 9.49 grams of the tetracid product was obtained as greenish yellow powder; 67% isolated yield, m.p. 312-316° C. $^1$H NMR (400 MHz, $d_6$-acetone): δ=7.94 (s, 2H), 7.85-7.88 (m, 4H), 7.72-7.76 (t, J=7.6 Hz, 2H), 7.52-7.55 (m, 2H).

(b) Synthesis of 4,4'-(2-fluoro-1,4-phenylene)bis(ethyne-2,1-diyl)diphthalic anhydride: To a 100 mL round-bottomed flask equipped with a stirrer bar and a condenser connected to a nitrogen inlet, 8.50 g 18.0 mmol) of 4,4'-(2-fluoro-1,4-phenylene)bis(ethyne-2,1-diyl) diphthalic acid, and 50 mL of acetic anhydride were charged. The reaction mixture was heated to reflux, and held at that condition for 3 hours. After cooling to room temperature, solids in the reaction mixture were collected via filtration, and washed with fresh acetic anhydride, ethyl acetate and hexanes. The product was vacuum-dried at 150° C., 0.5 torr for 24 hours. 6.98 g of greenish yellow powder was obtained in 89.3% isolated yield, m.p. 313.6-317.2° C. $^1$H NMR (400 MHz, $d_6$-acetone): δ=8.25-8.26 (m, 2H), 8.19-8.21 (ddd, J=1.6, 3.2, 8.0 Hz, 2H), 7.79-7.83 (t, J=7.6 Hz, 2H), 7.58-7.62 (td, J=1.6, 7.0 Hz, 2H). FT-IR (cm$^{-1}$): 3079, 3050, 2217, 1852, 1839, 1171, 1611, 1544, 1507, 1429, 1412, 1429, 1325, 1257, 1237, 1105, 933, 898, 736, 670. Elemental analysis calculated for $C_{29}H_9FO_6$, C, 71.57; H, 2.08 O, 22.00. Found: C, 71.37; H, 2.06; O, 22.45.

Example 3 4'-((3,4-dicarboxyphenyl)ethynyl)biphenyl-3,4-dicarboxylic dianhydride (PE-DPA)

(a) Synthesis of biphenyl-3,4-dicarboxylic acid: To a 500 mL round-bottomed flask equipped with a magnetic stir bar and a condenser connected to a nitrogen inlet, 21.80 g (0.10 mol) of 4-bromophthalic anhydride and 150 mL of ethanol were charged. To the mixture, 41.8 mL of triethylamine was added slowly. The mixture was then stirred at room temperature for 1 hour, and 13.41 g (0.11 mol) of phenyl boronic acid, 0.701 g (1.0 mmol) of bis(triphenylphosphine)palladium dichloride and 0.524 mg (2.0 mmol) of triphenylphosphine were added. The reaction mixture was heated in an oil bath at 90° C. for 16 hours. After cooled to room temperature, ethanol and excess triethylamine were removed by rotary evaporation. 200 mL of toluene was added to the mixture. White solids were removed by filtration. After acetone removed under vacuum, the residual was a dark brownish, viscous liquid. To this liquid, 12.00 g (0.30 mol) of sodium hydroxide in 300 mL of water was added. The mixture was stirred at room temperature for 72 hours. 200 mL of water was added to the mixture. Solids were removed via filtration. The filtrate was neutralized with concentrated hydrochloric acid to pH around 2. The mixture was extracted with 150 mL ethyl acetate for three times. The ethyl acetate extract was washed with 3×150 mL of de-ionized water. After ethyl acetate had been removed by rotary evaporation, the residual was boiled in 2×200 mL of hot toluene and filtered at room temperature. 16.0 g rams final product was obtained as near white powder, m.p. 192.8-195.0° C., 66.1% isolated yield. $^1$H NMR (400 MHz, $d_6$-acetone): δ=7.99 (brs, 1H), 7.89 (brs, 2H), 7.74-7.76 (d, J=8.8 Hz, 2H), 7.49-7.53 (t, J=8.0 Hz, 2H), 7.41-7.45 (t, J=8.8 Hz, 1H).

(b) Synthesis of 4'-Iodobiphenyl-3,4-dicarboxylic acid: To a 100 mL round-bottomed flask equipped with a magnetic stir bar, 20 mL of 98% concentrated sulfuric acid and 1.08 g (5.03 mmol) of sodium periodate were charged. To this mixture, 2.25 g (15.0 mmol) of sodium iodide were added slowly within 30 minutes. After the addition of sodium iodide, the mixture was stirred for another hour. To a 300 mL round-bottomed flask equipped with a magnetic stir bar, 4.84 g (20.0 mmol) of biphenyl-3,4-dicarboxylic acid, and 98% concentrate sulfuric acid were charged. To the mixture, above made iodonium solution was added slowly within 30 minutes. The mixture was further stirred for 2 hours, then, poured onto 200 g ice. Solids were harvested by filtration. The solids were resolved in ethyl acetate, washed with sodium bisulfite, water. After ethyl acetate was removed under reduced pressure, 7.10 grams of final product was obtained as near white solids, 96.4% isolated yield, m.p. 171.5-174.7° C. $^1$H NMR (400 MHz, $d_6$-acetone): δ=7.99 (d, J=1.2 Hz, 1H), 7.87-7.90 (m, 4H), 7.56-7.58 (d, J=8.4 Hz, 2H), 1.95 (s, 2H). (c) Synthesis of 4'-((3,4-dicarboxyphenyl)ethynyl)biphenyl-3,4-dicarboxylic acid: To a 300 mL round bottom flask equipped with magnetic stir bar, condenser and nitrogen inlet, 9.20 (25.0 mmol) 4'-Iodobiphenyl-3,4-dicarboxylic acid, 5.70 g (30.0 mmol) 4-ethynylphthalic acid, 47.6 mg (0.425 mmol) copper iodide and 177.7 mg (0.25 mmol) bis(triphenylphosphine) palladium dichloride were charged. After vacuum and back fill with nitrogen three times, 25 mL trimethylamine and 75 mL tetrahydrofuran were charged. The mixture stirred at room temperature for 72 hours. Low boiling point liquids were removed under reduced pressure. The residue was dissolved in water, and filtrated. The filtrate was neutralized by hydrochloric acid until solution pH is below 2. Solids were harvested, washed with deionized water, air dried. The solids were suspended in hot ethyl acetate, after cooled to room temperature, solids were collected by filtration. 9.5 grams of product was obtained as light brow powder, 76.1% isolated yield, m.p. 287-291° C. $^1$H NMR (400 MHz, $d_6$-DMSO): δ=13.7 (broad, 4H), 8.01 (broad, 1H), 7.91-7.35 (m, 2H), 7.81-7.85 (m, 4H), 7.71-7.76 (m, 3H). (d) 4'-((3,4-dicarboxyphenyl)ethynyl)biphenyl-3,4-dicarboxylic dianhydride (PE-DPA): To a 100 mL round bottom flask equipped with stirrer bar, condenser, and nitrogen inlet, 8.60 g 20.0 mmol) 4'-((3,4-dicarboxyphenyl)ethynyl)biphenyl-3,4-dicarboxylic acid and 50 mL acetic anhydride were charged. The mixture was heated to reflux and held for 3 hours. After cooled to room temperature, solids were harvested via filtration and washed with fresh acetic anhydride, ethyl acetate and hexanes. The product was vacuum dried at 150° C., 0.5 torr for 24 hours. 6.00 g greenish yellow powder was obtained, 76.1% isolated yield, m.p. 297.9-300.1° C. $^1$H NMR (400 MHz, $d_6$-acetone): δ=8.39-8.41 (m, 2H), 8.24 (s, 1H), 8.18-8.21 (m, 2H), 8.13-8.15 (dd, J=0.8, 8.0 Hz, 1H), 8.00-8.03 (d, J=8.4 Hz, 2H), 7.84-7.86 (d, J=8.4 Hz, 2H). FT-IR ($cm^{-1}$): 3078, 2214, 1843, 1767, 1610, 1489, 1430, 1411, 1325, 1241, 1103, 890, 826, 736. Elemental analysis calculated for $C_{24}H_{10}O_6$, C, 73.10; H, 2.56; O, 24.34. Found: C, 73.05; H, 2.55; O, 24.70.

Example 4 4,4'-(biphenyl-4,4'-diylbis(ethyne-2,1-diyl))diphthalic anhydride (EPPE-DPA). (a) Synthesis of 4,4'-(biphenyl-4,4'-diylbis(ethyne-2,1-diyl))diphthalic acid: To a 300 mL round bottom flask equipped with stir bar and nitrogen inlet, 9.13 g (48.0 mmol) 4-ethynylphthalic acid, 8.12 g (20.0 mmol) 4,4'-diiodobiphenyl, 38.1 mg (0.2 mmol) copper iodide, and 140.4 mg (0.2 mmol) bis(triphenylphosphine)palladium dichloride were charged After vacuum-back-fill with nitrogen three times, 30 mL trimethylamine and 90 mL tetrahydrofuran (THF) were charged. The mixture stirred at room temperature for 72 hours. After removing solvents under reduced pressure, the residue was dissolved water, and filtrated. The filtrate was neutralized with hydrochloric acid until pH is below 2. Solids were harvested via filtration and washed with de-ionized water, then isopropanol. After air drying, the solids were suspended in 150 mL THF and heated to reflux. Heating was continued for another 30 mins. After the reaction mixture had cooled to room temperature, it was filtered and 7.35 grams of final product was obtained as greenish yellow solids, 69.3% isolated yield, m.p. 342-345° C. $^1$H NMR (400 MHz, $d_6$-acetone): δ=7.92 (d, J=1.2 Hz, 2H), 7.78-7.87 (m, 8H), 7.72-7.74 (d, J=8.4 Hz, 2H), 1.95 (d, 4H). (b) Synthesis of 4,4'-(biphenyl-4,4'-diylbis(ethyne-2,1-diyl))diphthalic anhydride: To a 100 mL round-bottomed flask equipped with a stirrer bar and a condenser connected to a nitrogen inlet, 7.43 g (14.0 mmol) of 4,4'-(biphenyl-4,4'-diylbis(ethyne-2,1-diyl))diphthalic acid and 30 mL acetic anhydride were charged. The mixture was refluxed for 3 hours. After the reaction mixture had cooled to room temperature, the dianhydride product was collected by filtration, followed by washing with acetic anhydride, ethyl acetate and hexanes. After vacuum drying at 150° C., 0.5 torr for 24 hours, 6.75 g of the dianhydride was obtained as a greenish yellow powder in 97.5% isolated yield, m.p. 342-345° C. $^1$H NMR (400 MHz, $d_6$-acetone): δ=8.22-8.23 (m, 2H), 8.17-8.20 (dd, J=1.2, 8.0 Hz, 2H), 8.12-8.15 (dd, J=0.8, 8.0 Hz, 2H), 7.86-7.88 (d, J=1.2, 6.8 Hz, 4H), 7.74-7.80 (d, J=6.8 Hz, 4H). FT-IR ($cm^{-1}$): 3073, 2206, 1843, 1819, 1769, 1614, 1603, 1500, 1431, 1401, 1321, 1262, 1246, 1135, 1105, 1083, 1002, 933, 891, 820, 736, 702, 672, 641, 609, 572, 520, 460. Elemental analysis calculated for $C_{32}H_{14}O_6$, C, 77.73; H, 2.85; O, 19.49. Found: C, 77.59; H, 2.82; O, 19.49.

Example 5 4,4'-(1,3-phenylenebis(ethyne-2,1-diyl))diphthalic anhydride (1,3EPE-DPA). (a) Synthesis of 4,4'-(1,3-phenylenebis(ethyne-2,1-diyl))diphthalic acid: To a 300 mL round bottom flask equipped with stir bar and nitrogen inlet, 12.00 g (63. mmol) 4-ethynylphthalic acid, 9.90 g (30.0 mmol) 1,3-diiodobenzene, 57.1 mg (0.3 mmol) copper iodide, and 210.6 mg (0.3 mmol) bis(triphenylphosphine) palladium dichloride were charged. After vacuum-back-fill with nitrogen three times, 30 mL of triethylamine and 90 mL tetrahydrofuran (THF) were charged. The mixture stirred at room temperature for 72 hours. After removing solvents by rotary evaporation, the residue was dissolved water, and filtered. The filtrate was neutralized with hydrochloric acid until pH is below 2. The mixture was extracted with ethyl acetate. After ethyl acetate had been removed, the crude product was purified by silica gel column chromatography, first using ethyl acetate/heptane, and then ethyl acetate as eluents. After column chromatography, the obtained solids were suspended in 30 mL of hot ethyl acetate, and upon cooling down to room temperature the heterogeneous mixture was filtered. 6.7 grams of product was obtained as a 1:1 complex of product with ethyl acetate, in 41.2% isolated yield, m.p. 271.0-275.0° C. $^1$H NMR (400 MHz, $d_6$-acetone): δ=7.93 (m, 2H), 7.84-7.86 (m, 3H), 7.79-7.81 (dd, J=1.2, 8.0 Hz, 2H), 7.65-7.67 (m, 2H), 7.50-7.54 (t, J=8.0 Hz, 1H). (b) Synthesis of 4,4'-(1,3-phenylenebis(ethyne-2,1-diyl))diphthalic anhydride: To a 100 mL round bottom flask equipped with stirrer bar, condenser, and nitrogen inlet, 5.97 g (13.2 mmol) 4,4'-(1,3-phenylenebis(ethyne-2,1-diyl)) diphthalic acid and 25 mL acetic anhydride were charged. The mixture was heated to reflux and held for 3 hours. After cooled to room temperature, solids were harvested via filtration and washed with fresh acetic anhydride, ethyl acetate and hexanes. The product was vacuum dried at 150° C., 0.5 torr for 24 hours. 4.20 g of light yellow powder was obtained, m.p. 277.9-279.8° C., 76.1% isolated yield. $^1$H NMR (400 MHz, $d_6$-acetone): δ=8.24 (s, 2H), 8.18-8.21 (dd, J=1.2, 8.0 Hz, 2H), 8.13-8.15 (d, J=8.0 Hz, 2H), 7.94 (t, J=1.2 Hz, 1H) 7.75-7.77 (dd, J=1.6, 7.6 Hz, 2H), 7.58-7.62 (t, J=7.6 Hz, 1H). FT-IR ($cm^{-1}$): 3097, 3077, 3057, 2218, 1840, 1767, 1610, 1489, 1431, 1323, 1308, 1253, 1237, 1104, 1082, 900, 887, 795, 734. 688. Elemental analysis calculated for $C_{26}H_{10}O_6$, C, 74.64; H, 2.41; O, 22.95. Found: C, 74.60; H, 2.38; O, 22.90.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and process, and illustrative examples shown and described. Accordingly, departures may be made from such details without departing from the scope of the general inventive concept.

What is claimed is:

1. A process of making a monomer, said process comprising:
   a.) thermally dehydrating, at temperature from about 150° C. to about 200° C., a molecule or a mixture of molecules having the following formula:

or b.) chemically dehydrating a molecule or a mixture of molecules having the following formula:

by contacting said molecule or mixture of molecules with acetic anhydride to yield a monomer or mixture of monomers having the following formula:

2. The process of claim 1 wherein said dehydration temperature is from about 150° C. to about 180° C.

3. A molecule having one of the following structures:

* * * * *